United States Patent [19]

Albarda et al.

[11] Patent Number: 4,464,926
[45] Date of Patent: Aug. 14, 1984

[54] METHOD AND APPARATUS FOR SENSING THE PRESENCE OF OXYGEN IN A GAS MIXTURE

[75] Inventors: Scato Albarda, Gross Schenkenberg; Alfred Eder, Munich, both of Fed. Rep. of Germany

[73] Assignee: Drägerwerk Aktiengesellschaft, Fed. Rep. of Germany

[21] Appl. No.: 438,716

[22] Filed: Nov. 3, 1982

[30] Foreign Application Priority Data

Nov. 17, 1981 [DE] Fed. Rep. of Germany ....... 3145542

[51] Int. Cl.³ ............................................ G01N 27/00
[52] U.S. Cl. ..................................... 73/27 A; 324/204
[58] Field of Search ...................... 73/27 A, 27 R, 23; 324/204

[56] References Cited

U.S. PATENT DOCUMENTS 2,729,097  1/1956  Cherrier ............................. 73/27 A
2,957,128 10/1960  Spry ..................................... 324/204
3,479,860 11/1969  Luft ..................................... 73/27 A Primary Examiner—Donald O. Woodiel
Assistant Examiner—Vincent P. Kovalick
Attorney, Agent, or Firm—McGlew and Tuttle

[57] ABSTRACT

A sensor for sensing the presence of oxygen in a test gas mixture comprises either first or second tubes for the separate flow of a measured gas and a gas to be tested for a single tubular arrangement for the successive flow of these two gases in association with a plurality of radio-frequency coils which are connected in an electrical bridge circuit to that they can be balanced in any variation of the inductance measure. Since oxygen in the gas produces a paramagnetism which provides induction variations in the coils of the balancing circuit, the variations of the balancing circuit may be used to sense the proportion of the oxygen content in the gases. With the inventive method the gases are passed into association with the balancing circuit and variations of the test gas from the measured gas are sensed by the circuit balance which is produced by the oxygen which is present in the gas mixtures. Such a sensor may be used for breath protection, diving and medical fields.

8 Claims, 4 Drawing Figures

METHOD AND APPARATUS FOR SENSING THE PRESENCE OF OXYGEN IN A GAS MIXTURE

FIELD AND BACKGROUND OF THE INVENTION

This invention relates in general to gas sensing devices and in particular to a new and useful device for sensing oxygen content in a gas mixture as a result of the variations of paramagnetism producing induction variations in a bridge circuit.

Oxygen is used in many gas reactions as reactant and in respiratory apparatus as an important gas component. For a long time, there is a need for continuously determining the $O_2$ concentration in the various streams and reaction stages. Since the other gas components may strongly differ in their nature and concentration, an analyzer is wanted which is as selective as possible.

An oxygen property of interest in this regard is its paramagnetic susceptibility which in many respects by far exceeds that of most of the technological gases. Therefore, $O_2$ measuring methods based on magnetism are predominant. The three most employed are:

(a) the thermomagnetic method,
(b) the method based on the principle of so called "Remling's" magnetic torsion balance, and
(c) the rise equilibrium method.

Apparatus according to (a) have proved as rugged and reliable measuring devices. However, they have the disadvantage that accompanying gases, especially at low concentrations, invalidate the measurement, depending on the nature and concentration of the gas.

"Remling's" magnetic torsion balance according to (b), comprises two thin-walled balls which are connected to each other by thin rods and suspended from a torsion thread in a field produced by two magnet pole couples. The magnet poles and the balls are enclosed in a measuring chamber. The angle of deviation is a measure of the $O_2$ content in the measured gas. The difficulties with a torsion balance method arise from the extraordinarily small torsional moment to be measured and the sensitivity of the apparatus to external shocks and vibrations.

In the rise equilibrium method according to (c), a gas stream to be measured and an $O_2$-free reference gas stream are introduced into a magnetic field, and the differential pressure between the inlet connections and the two streams is measured. It is disadvantageous that the differential pressure to be measured is very small. A particular advantage, however, is the quick response to rapid concentration variations in the measured gas.

Still another method is known, utilizing the paramagnetic property of oxygen. In this method, the gas mixture is introduced in the interior of a radio-frequency coil and serves virtually as a coil core. Consequently, the self-inductance of the coil varies in accordance with the proportion of paramagnetic components. This variation of the self-inductance of the coil brings a radio-frequency circuit out of tune, and the amount of detuning is a measure of the proportion of paramagnetic substances. What is disadvantageous in this method is the small amount of the effect to be utilized, and the measuring difficulties resulting therefrom (German Pat. No. 871539).

SUMMARY OF THE INVENTION

The invention is directed to a small-size paramagnetic $O_2$ sensor operating in accordance with the above method, being little responsive to ambient disturbing effects, and accomplishing accurate measurement and indication over a wide measuring range.

In accordance with the invention the sensor for sensing the presence of oxygen in a test gas mixture comprises an arrangement of a flow device with a separate successive flow of a test gas and a measured gas or for the combined flow of a test and measured gas in an arrangement including a plurality of radio-frequency coils in the flow path which are connected to an electrical bridge circuit so that the variations in the flow of oxygen through the conductive fields of the radio-frequency coils produce variations in the bridge circuit which will indicate the amount of oxygen present. With the inventive method, test gas and a measured gas may be passed simultaneously through spaced apart tubes which are arranged in a housing and which are surrounded by radio-frequency coils which are interconnected in a bridge circuit in an arrangement wherein the reference gas which is passed through its tube will vary the circuit over that produced by the measured gas flow through its tube in accordance with the amount of oxygen which is present therein.

The invention provides a paramagnetic oxygen sensor which is well suited for selective measuring of oxygen in gas mixtures due to the strongly marked paramagnetism of oxygen as compared to other gases. This paramagnetism causes inductance variations in the field of a radio-frequency coil. Such a variation is only relatively weak and for this reason it is essential to minimize interfering disturbances. In one embodiment a plurality of radio-frequency coils are accommodated in a thermally and mechanically shielded manner in a housing and are well thermally coupled to each other. They are operated as a bridge circuit and their induction fields extend through both the gas stream to be measured and the reference gas stream. The coils are thermally stable and designed as printed silver coils carried on ceramic substrates. Both the measured and the reference gas are connected through mirror coated quartz tubes which are gastightly insulated relative to the coils. In one embodiment the tubes extend through the coils and in another embodiment the coils are provided on both sides of a rotating plate and the tubes extend alongside the plate within the induction field.

The inventive $O_2$ sensor comprises coils producing an induction field in the gas to be measured and in a reference gas. The coils are connected in a bridge circuit, so that the effect of measurement is obtained without disturbances. The good thermal coupling of the individual coils to each other with at the same time their satisfactory thermal and mechanical uncoupling from the ambience, substantially eliminates any changes which would result therefrom; should residuals still remain, they will be equal for all the coils.

Accordingly, it is an object of the invention to provide a sensor for sensing the presence of oxygen in a test gas mixture which comprises a flow tube arrangement for the passage of test and measured gas, a plurality of radio-frequency coils associated with said flow tube arrangement which are connected in an electrical bridge circuit and wherein the oxygen and the gas produces a paramagnetism producing induction variations in the coils which are in proportion to the content of the oxygen and which are indicated in the circuit.

In accordance with the inventive method a gas to be measured is passed through a tube along with a measured gas and a radio-frequency coil arrangement is disposed to produce a paramagnetic field in the vicinity of the tube accommodating the gas flow and wherein the oxygen in the gas produces a paramagnetism causing induction variations in the coils and in measuring the variations in the coils as an indication of the amount of oxygen present in the gas.

A further object of the invention is to provide a sensor which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
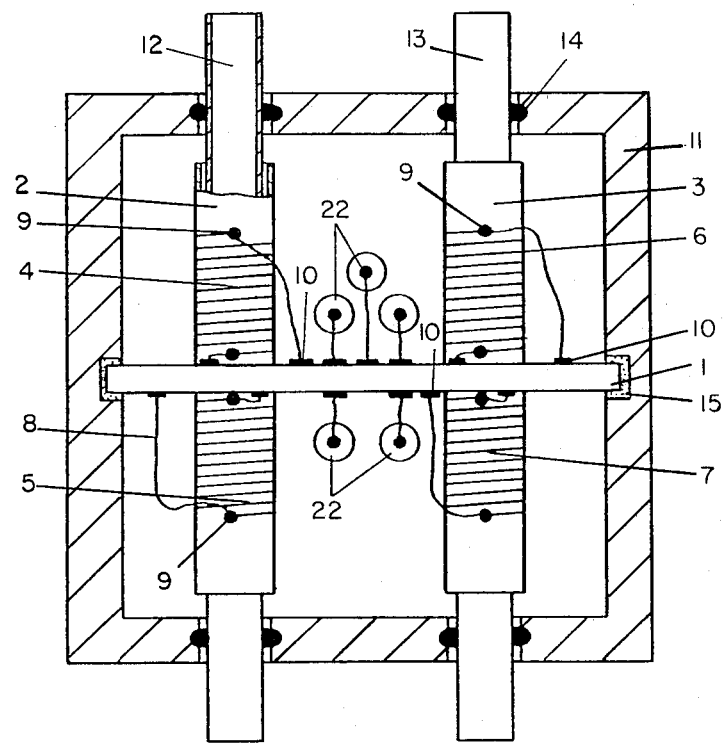
FIG. 1 is a diagrammatical sectional view of a paramagnetic oxygen sensor constructed in accordance with the invention.
Figure 2:
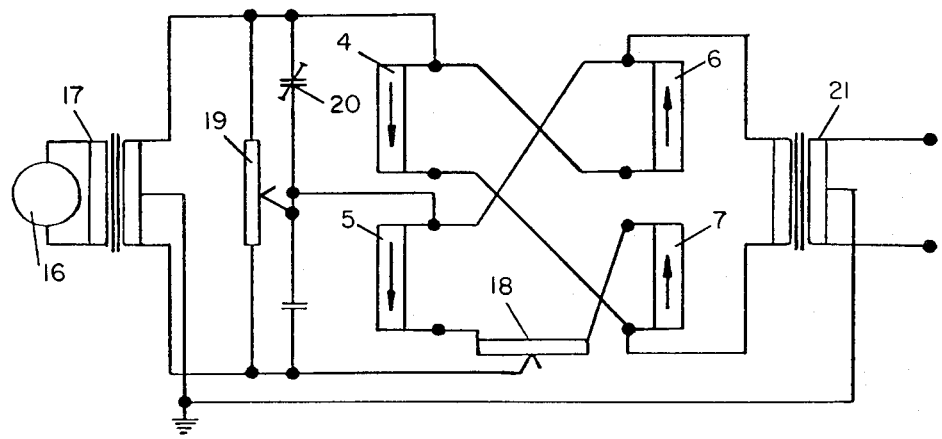
FIG. 2 is a circuit diagram used with the sensor shown in FIG. 1.

Referring to the drawings in particular the invention embodied therein in FIG. 1 and 2, comprises a sensor for sensing the presence of oxygen in a test gas mixture which comprises a gas flow tube arrangement which in the embodiment illustrated comprises a first flow tube 12 for a test gas to be measured and a second flow tube 13 adjacent the first flow tube for a measured gas. A plurality of radio-frequency coils 4 and 5, and 6 and 7 associated with the respective tubes is connected in an electrical bridge circuit as indicated in FIG. 2. The oxygen in the respective gases which are passed through the respective tubes produces a paramagnetism causing induction variations in the coils of the circuit in proportion to the oxygen content which is indicated in the circuit.

The paramagnetic $O_2$ sensor according to FIG. 1 comprises a ceramic carrier plate 1 supporting ceramic coil forms 2 and 3. Coils 4 and 5 are provided on coil form 2, and coils 6 and 7 are provided on coil form 3. The coils are advantageously produced by inserting high-conductivity silver paste into grooves provided in the coil forms 2 and 3 and burning it on. The coils are connected through bond wires 8 extending between bosses 9 of the coils and connection areas 10 on the carrier plate 1. Carrier plate 1 supporting the coil groups is inserted in a housing 11 of well-conducting material such as aluminum. To compensate for thermal expansion, a strip 15 of elastic material is provided between carrier plate 1 and housing 11.

A tube 12 for a gas to be measured and a tube 13 for a reference gas extend in a contact-free manner through the respective coil forms 2 and 3 and are gastightly supported in housing 11. Both tubes 12 and 13 are made of mirror-coated quartz glass. To obtain an optimum thermal uncoupling between the tubes and assembled coil forms 2 and 3, housing 11 is either evacuated or filled with a suitable gas.

The circuit diagram of FIG. 2 shows how coils 4, 5, 6 and 7 are interconnected to a bridge. The bridge is supplied through an input transformer 17 from an oscillator 16. A coil 18 is provided for balancing the inductance, while a resistor 19 and a capacitor 20 are provided to balance the leaky or stray capacitor. The bridge is tuned out through an output transformer 21. Grounded center tapping of transformers 17 and 21 results in a substantially symmetric signal. The supply and terminal parts are accommodated in spaces (not shown) below housing 11 and their connections pass through tight bushings 22.

Figure 3:
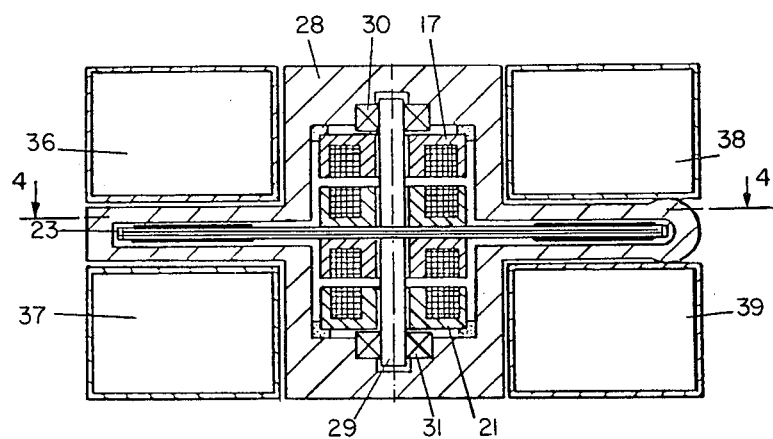
FIG. 3 is a sectional view of another embodiment of paramagnetic oxygen sensor.
Figure 4:
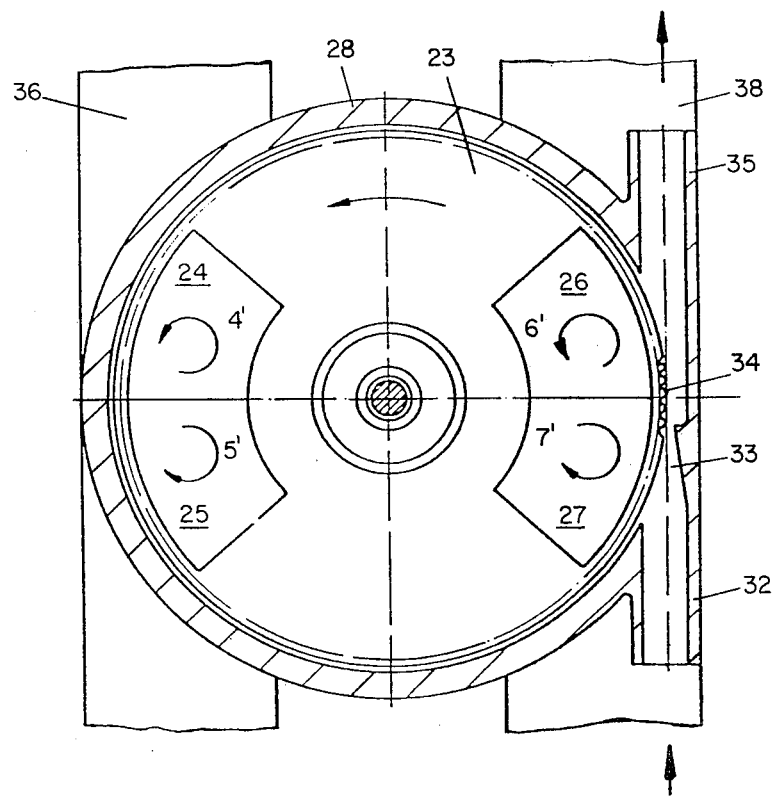
FIG. 4 is a section taken along the line 4—4 of FIG. 3.

FIGS. 3 and 4 show an $O_2$ sensor designed with flat coils. A carrier plate 23 supports in segments 24, 25, 26, 27 flat coils 4', 5', 6', 7' which are interconnected in accordance with FIG. 2. The arrows indicate the winding directions. The primaries of transformsers 17 and 21 are mounted on plate 23, the secondaries thereof in a housing 28. Plate 23 comprises a rotatable shaft 29 which is mounted for rotation in ball bearings 30 and 31 supported in housing 28.

In operation, plate 23 is set in rotation. The drive means is compressed air. The air enters through an inlet tube 32 supported by housing 28, is accelerated in a throat 33, skirts a knurling 34 provided on the outer circumference of plate 23, and expands to leave housing 28 through an outlet tube 35. With a diameter about 50 mm, plate 23 rotates at a speed of 6,000 to 18,000 rpm. The field of coils 4–7 extends both through tubes 36 and 37 conducting the gas to be measured, and through tubes 38 and 39 conducting the reference gas. Other well known mechanisms may also be used for driving plate 23.

While specific embodiments of the invention have been shown and described in detail to illustrate the application of the principles of the invention, it will be understood that the invention may be embodied otherwise without departing from such principles.

What is claimed is:

1. A sensor for sensing the presence of oxygen in a test gas mixture, comprising a separate flow tube for the passage of a test gas and a measured gas, a plurality of radio-frequency coils associated with each of said flow tubes, an electrical bridge circuit interconnecting said radio-frequency coils, the oxygen in the gas flowing through said flow tube means producing a paramagnetism causing induction variations in said coils of said circuit in proportion to the content of the oxygen which are indicated in said circuit.

2. A sensor for sensing the presence of oxygen in a test gas mixture, comprising flow tube means for the passage of a test gas and a measured gas, a plurality of radio-frequency coils associated with said flow tube, an electrical bridge circuit interconnecting said radio-frequency coils, the oxygen in the gas flowing through said flow tube means producing a paramagnetism causing induction variations in said coils of said circuit in proportion to the content of the oxygen which are indicated in said circuit, said flow tube means comprising a first flow tube for a test gas to be measured and a second flow tube adjacent said flow tube for a measured gas, said plurality of radio-frequency coils including a ceramic carrier plate,, a housing surrounding said carrier plate and supporting said plate therein, a first coil form having printed coils thereon, a second coil form having printed coils thereon, both of said first and second coils being supported on said carrier plate, means separating said carrier plate thermally from said housing, seal ring means sealing said flow tubes with said housing at the entrance and exit therefrom.

3. A sensor according to claim 2, wherein said flow tubes are made of a mirror coated quartz glass.

4. A sensor according to claim 2 including a rotating plate mounted in said housing, said radio-frequency coils being located at a side of said plate, said flow tubes being mounted on said housing so as to extend through susceptive induction field of said coils.

5. A sensor according to claim 2, wherein said coils comprise a high conductivity silver paste mounted on said ceramic carrier.

6. A sensor for sensing the presence of oxygen comprising a housing, a ceramic carrying plate mounted in said housing and insulated therefrom, first and second mirror finished quartz glass tubes extending through said housing transverse to said plate and being sealed with said housing at the entrance and exit therefrom, a plurality of coils wound around each of said tubes and having terminals from said coils to said carrier plate and an electrical bridge circuit connected to said coils.

7. A sensor for sensing the presence of oxygen in a test gas comprising a housing having at least one gas passage for a test gas and one gas passage for a measured gas extending therethrough, a plate rotatably mounted in said housing adjacent said gas passage, a plurality of radio-frequency coils mounted on said plate for rotation therewith, means defining a driving gas passage intercepting the periphery of said plate, said plate having a knurled circumference, a nozzle throat defined in said driving gas passage for directing gas against the knurled surface of said plate to rotate said plate.

8. A method of sensing the presence of oxygen in a test gas mixture using a first tube element for the flow of the measured gas and a second tube element for the flow of a reference gas therethrough and a radio-frequency coil disposed around each tube element and connected in a bridge circuit, comprising directing the reference gas through the reference gas tube element so as to move the gas in the vicinity of one of the fields generated by the radio-frequency coils, balancing the bridge circuit, passing the reference gas to the other tube element in the vicinity of another of the fields generated by the radio-frequency coils so as to cause the oxygen in the reference gas to produce a paramagnetic and induction variation in the coils in proportion to the content of the oxygen, and observing the bridge circuit on balance as an indication of the presence of the oxygen.

* * * * *